(12) United States Patent
Johnson et al.

(10) Patent No.: US 10,531,917 B2
(45) Date of Patent: Jan. 14, 2020

(54) SYSTEMS AND METHODS FOR ENERGY DELIVERY

(71) Applicant: NeuWave Medical, Inc., Madison, WI (US)

(72) Inventors: Scott Johnson, Madison, WI (US); Patrick Moran, Madison, WI (US); David Anderson, Madison, WI (US); Richard W. Schefelker, Madison, WI (US); Christopher L. Brace, Madison, WI (US)

(73) Assignee: NEUWAVE MEDICAL, INC., Madison, WI (US)

( * ) Notice: Subject to any disclaimer, the term of this patent is extended or adjusted under 35 U.S.C. 154(b) by 223 days.

(21) Appl. No.: 15/487,128

(22) Filed: Apr. 13, 2017

(65) Prior Publication Data
US 2017/0296268 A1    Oct. 19, 2017

Related U.S. Application Data

(60) Provisional application No. 62/323,319, filed on Apr. 15, 2016.

(51) Int. Cl.
*A61B 18/12* (2006.01)
*A61B 18/18* (2006.01)
(Continued)

(52) U.S. Cl.
CPC ......... *A61B 18/1815* (2013.01); *A61B 18/14* (2013.01); *A61B 2018/00005* (2013.01);
(Continued)

(58) Field of Classification Search
CPC ............. A61B 18/14; A61B 18/1815; A61B 2018/00005; A61B 2018/00577;
(Continued)

(56) References Cited

U.S. PATENT DOCUMENTS

| | | |
|---|---|---|
| 3,800,552 A | 4/1974 | Sollami |
| 3,838,242 A | 9/1974 | Goucher |

(Continued)

FOREIGN PATENT DOCUMENTS

| | | |
|---|---|---|
| AU | 2015/202149 | 5/2015 |
| CN | 2579361 | 10/2003 |

(Continued)

OTHER PUBLICATIONS

European Search Report, EP Patent Application No. 17168163.8, dated Sep. 13, 2017.
(Continued)

*Primary Examiner* — Thomas A Giuliani
*Assistant Examiner* — Catherine C. Premraj
(74) *Attorney, Agent, or Firm* — Casimir Jones, SC; Robert Goetz

(57) ABSTRACT

The present invention relates to comprehensive systems and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems and methods are provided for identifying and treating a target tissue region adjusting for ablation-related anatomical changes (e.g., tissue contraction).

11 Claims, 1 Drawing Sheet

(51) Int. Cl.
*A61B 18/14* (2006.01)
*A61B 18/00* (2006.01)

(52) U.S. Cl.
CPC ............ *A61B 2018/00589* (2013.01); *A61B 2018/00595* (2013.01); *A61B 2018/00791* (2013.01); *A61B 2018/00898* (2013.01); *A61B 2018/00982* (2013.01)

(58) Field of Classification Search
CPC .......................................... A61B 2018/00589; A61B 2018/00595; A61B 2018/00791; A61B 2018/00898; A61B 2018/00904; A61B 2018/00982
See application file for complete search history.

(56) References Cited

U.S. PATENT DOCUMENTS

| | | |
|---|---|---|
| 3,991,770 A | 11/1976 | LeVeen |
| 4,057,064 A | 11/1977 | Morrison |
| 4,074,718 A | 2/1978 | Morrison |
| 4,312,364 A | 1/1982 | Convert |
| 4,375,220 A | 3/1983 | Matvias |
| 4,446,874 A | 5/1984 | Vaguine |
| 4,494,539 A | 1/1985 | Zenitani |
| 4,534,347 A | 8/1985 | Taylor |
| 4,557,272 A | 12/1985 | Carr |
| 4,586,491 A | 5/1986 | Carpenter |
| 4,589,424 A | 5/1986 | Vaguine |
| 4,601,296 A | 7/1986 | Yerushalmi et al. |
| 4,621,642 A | 11/1986 | Chen |
| 4,627,435 A | 12/1986 | Hoskin |
| 4,641,649 A | 2/1987 | Walinsky |
| 4,643,186 A | 2/1987 | Rosen |
| 4,662,383 A | 5/1987 | Sogawa |
| 4,700,716 A | 10/1987 | Kasevich |
| 4,712,559 A | 12/1987 | Turner |
| 4,776,086 A | 10/1988 | Kasevich |
| 4,790,311 A | 12/1988 | Ruiz |
| 4,800,899 A | 1/1989 | Elliott et al. |
| 4,860,752 A | 8/1989 | Turner |
| 4,880,015 A | 11/1989 | Nierman |
| 4,901,719 A | 2/1990 | Trenconsky |
| 4,945,912 A | 8/1990 | Langberg |
| 4,974,587 A | 12/1990 | Turner et al. |
| 5,007,437 A | 4/1991 | Sterzer |
| 5,026,959 A | 6/1991 | Ito |
| 5,057,104 A | 10/1991 | Chess |
| 5,057,106 A | 10/1991 | Kasevich |
| 5,074,861 A | 12/1991 | Schneider |
| RE33,791 E | 1/1992 | Carr |
| 5,098,429 A | 3/1992 | Sterzer |
| 5,129,396 A | 7/1992 | Rosen |
| 5,150,717 A | 9/1992 | Rosen |
| 5,167,619 A | 12/1992 | Wuchinich |
| 5,211,625 A | 5/1993 | Sakurai |
| 5,213,561 A | 5/1993 | Weinstein et al. |
| 5,246,438 A | 9/1993 | Langberg |
| 5,248,312 A | 9/1993 | Langberg |
| 5,275,597 A | 1/1994 | Higgins |
| 5,277,201 A | 1/1994 | Stern |
| 5,281,213 A | 1/1994 | Milder |
| 5,281,217 A | 1/1994 | Edwards |
| 5,295,955 A | 3/1994 | Rosen |
| 5,300,099 A | 4/1994 | Rudie |
| 5,301,687 A | 4/1994 | Wong |
| 5,314,466 A | 5/1994 | Stern |
| 5,344,418 A | 9/1994 | Ghaffari |
| 5,344,435 A | 9/1994 | Turner |
| 5,348,554 A | 9/1994 | Imran |
| 5,358,515 A | 10/1994 | Hurter |
| 5,364,392 A | 11/1994 | Warner |
| 5,366,490 A | 11/1994 | Edwards |
| 5,369,251 A | 11/1994 | King |
| 5,370,678 A | 12/1994 | Edwards |
| 5,405,346 A | 4/1995 | Grundy |
| 5,431,649 A | 7/1995 | Mulier |
| 5,433,740 A | 7/1995 | Yamaguchi |
| 5,456,684 A | 10/1995 | Schmidt |
| 5,462,556 A | 10/1995 | Powers |
| 5,472,423 A | 12/1995 | Gronauer |
| 5,480,417 A | 1/1996 | Hascoet |
| 5,489,256 A | 2/1996 | Adair |
| 5,507,743 A | 4/1996 | Edwards |
| 5,531,677 A | 7/1996 | Lundquist |
| 5,540,649 A | 7/1996 | Bonnell et al. |
| 5,559,295 A | 9/1996 | Sheryll |
| 5,575,794 A | 11/1996 | Walus |
| 5,578,029 A | 11/1996 | Trelles |
| 5,591,227 A | 1/1997 | Dinh |
| 5,597,146 A | 1/1997 | Putman |
| 5,599,295 A | 2/1997 | Rosen |
| 5,599,352 A | 2/1997 | Dinh |
| 5,603,697 A | 2/1997 | Grundy |
| 5,620,479 A | 4/1997 | Diederich |
| 5,643,175 A | 7/1997 | Adair |
| 5,647,871 A | 7/1997 | Levine |
| 5,688,267 A | 11/1997 | Panescu |
| 5,693,082 A | 12/1997 | Warner |
| 5,697,949 A | 12/1997 | Giurtino |
| 5,716,389 A | 2/1998 | Walinsky |
| 5,737,384 A | 4/1998 | Fenn |
| 5,741,249 A | 4/1998 | Moss |
| 5,755,752 A | 5/1998 | Segal |
| 5,755,754 A | 5/1998 | Rudie |
| 5,759,200 A | 6/1998 | Azar |
| 5,776,129 A | 7/1998 | Mersch |
| 5,776,176 A | 7/1998 | Rudie |
| 5,782,827 A | 7/1998 | Gough |
| 5,788,692 A | 8/1998 | Campbell |
| 5,788,694 A | 8/1998 | Vancaillie |
| 5,800,494 A | 9/1998 | Campbell |
| 5,810,803 A | 9/1998 | Moss |
| 5,810,804 A | 9/1998 | Gough |
| 5,849,029 A | 12/1998 | Eckhouse |
| 5,902,251 A | 5/1999 | Vanhooydonk |
| 5,904,709 A | 5/1999 | Arndt et al. |
| 5,921,935 A | 7/1999 | Hickey |
| 5,957,969 A | 9/1999 | Warner |
| 5,963,082 A | 10/1999 | Dick |
| 5,995,875 A | 11/1999 | Blewett |
| 6,002,968 A | 12/1999 | Edwards |
| 6,012,457 A | 1/2000 | Lesh |
| 6,016,811 A | 1/2000 | Knopp |
| 6,026,331 A | 2/2000 | Feldberg |
| 6,044,846 A | 4/2000 | Edwards |
| 6,056,744 A | 5/2000 | Edwards |
| 6,067,475 A | 5/2000 | Graves |
| 6,073,052 A | 6/2000 | Zelickson |
| 6,083,255 A | 7/2000 | Laufer |
| 6,086,529 A | 7/2000 | Arndt |
| 6,091,995 A | 7/2000 | Ingle et al. |
| 6,097,985 A | 8/2000 | Kasevich |
| 6,102,885 A | 8/2000 | Bass |
| 6,104,959 A | 8/2000 | Spertell |
| 6,106,524 A | 8/2000 | Eggers |
| 6,120,496 A | 9/2000 | Whayne |
| 6,165,163 A | 12/2000 | Chien et al. |
| 6,174,307 B1 | 1/2001 | Daniel et al. |
| 6,182,666 B1 | 2/2001 | Dobak, III |
| 6,188,930 B1 | 2/2001 | Carson |
| 6,190,382 B1 | 2/2001 | Ormsby |
| 6,208,903 B1 | 3/2001 | Richards |
| 6,210,323 B1 | 4/2001 | Gilhuly et al. |
| 6,223,085 B1 | 4/2001 | Dann |
| 6,230,060 B1 | 5/2001 | Mawhinney |
| 6,235,022 B1 | 5/2001 | Hallock |
| 6,241,725 B1 | 6/2001 | Cosman |
| 6,245,062 B1 | 6/2001 | Berube |
| 6,246,784 B1 | 6/2001 | Summers |
| 6,246,905 B1 | 6/2001 | Mogul |
| 6,251,128 B1 | 6/2001 | Knopp |
| 6,254,598 B1 | 7/2001 | Edwards |
| 6,273,884 B1 | 8/2001 | Altshuler |
| 6,273,885 B1 | 8/2001 | Koop |

(56) References Cited

U.S. PATENT DOCUMENTS

| | | |
|---|---|---|
| 6,273,886 B1 | 8/2001 | Edwards |
| 6,277,113 B1 | 8/2001 | Berube |
| 6,287,302 B1 | 9/2001 | Berube |
| 6,306,130 B1 | 10/2001 | Anderson |
| 6,306,132 B1 | 10/2001 | Moorman |
| 6,312,427 B1 | 11/2001 | Berube |
| 6,325,796 B1 | 12/2001 | Berube |
| 6,347,251 B1 | 2/2002 | Deng |
| 6,355,033 B1 | 3/2002 | Moorman |
| 6,364,876 B1 | 4/2002 | Erb |
| 6,383,182 B1 | 5/2002 | Berube |
| 6,395,803 B1 | 5/2002 | Angeletakis |
| 6,398,781 B1 | 6/2002 | Goble |
| 6,402,742 B1 | 6/2002 | Blewett |
| 6,427,089 B1 | 7/2002 | Knowlton |
| 6,435,872 B1 | 8/2002 | Nagel |
| 6,461,351 B1 | 10/2002 | Woodruff et al. |
| 6,461,352 B2 | 10/2002 | Morgan |
| 6,471,696 B1 | 10/2002 | Berube |
| 6,500,174 B1 | 12/2002 | Maguire |
| 6,506,189 B1 | 1/2003 | Rittman |
| 6,514,249 B1 | 2/2003 | Maguire |
| 6,524,308 B1 | 2/2003 | Muller |
| 6,527,768 B2 | 3/2003 | Berube |
| 6,530,922 B2 | 3/2003 | Cosman |
| 6,546,077 B2 | 4/2003 | Chornenky |
| 6,575,969 B1 | 6/2003 | Rittman, III et al. |
| 6,577,903 B1 | 6/2003 | Cronin |
| 6,582,426 B2 | 6/2003 | Moorman et al. |
| 6,582,486 B1 | 6/2003 | Delpiano |
| 6,585,733 B2 | 7/2003 | Wellman |
| 6,593,395 B2 | 7/2003 | Angeletakis |
| 6,602,074 B1 | 8/2003 | Suh |
| 6,622,731 B2 | 9/2003 | Daniel |
| 6,635,055 B1 | 10/2003 | Cronin |
| 6,638,277 B2 | 10/2003 | Schaefer et al. |
| 6,652,520 B2 | 11/2003 | Moorman |
| 6,663,625 B1 | 12/2003 | Ormsby |
| 6,666,579 B2 | 12/2003 | Jensen |
| 6,673,068 B1 | 1/2004 | Berube |
| 6,683,625 B2 | 1/2004 | Muthusamy |
| 6,694,163 B1 | 2/2004 | Vining |
| 6,699,240 B2 | 3/2004 | Francischelli |
| 6,702,576 B2 | 3/2004 | Fischer |
| 6,709,271 B2 | 3/2004 | Yin |
| 6,740,107 B2 | 5/2004 | Loeb |
| 6,749,606 B2 | 6/2004 | Keast |
| 6,752,767 B2 | 6/2004 | Turovskiy |
| D493,531 S | 7/2004 | Padain |
| 6,770,070 B1 | 8/2004 | Balbierz |
| 6,780,178 B2 | 8/2004 | Palanker |
| 6,802,840 B2 | 10/2004 | Chin |
| 6,817,976 B2 | 11/2004 | Rovegno |
| 6,817,999 B2 | 11/2004 | Berube |
| 6,823,218 B2 | 11/2004 | Berube |
| 6,837,712 B2 | 1/2005 | Qian |
| 6,847,848 B2 | 1/2005 | Sterzer |
| 6,849,075 B2 | 2/2005 | Bertolero |
| 6,852,091 B2 | 2/2005 | Edwards |
| 6,866,624 B2 | 3/2005 | Chornenky |
| 6,866,663 B2 | 3/2005 | Edwards |
| 6,869,431 B2 | 3/2005 | Maguire et al. |
| 6,878,147 B2 | 4/2005 | Prakash |
| 6,890,968 B2 | 5/2005 | Angeletakis |
| 6,893,436 B2 | 5/2005 | Woodard |
| 6,898,454 B2 | 5/2005 | Atalar |
| D507,649 S | 7/2005 | Padain |
| 6,918,905 B2 | 7/2005 | Neuberger |
| 6,924,325 B2 | 8/2005 | Qian |
| 6,957,108 B2 | 10/2005 | Turner |
| 6,962,586 B2 | 11/2005 | Berube |
| 6,972,016 B2 | 12/2005 | Hill |
| 6,976,986 B2 | 12/2005 | Berube |
| 6,994,546 B2 | 2/2006 | Fischer |
| 7,022,105 B1 | 4/2006 | Edwards |
| 7,033,352 B1 | 4/2006 | Gauthier |
| 7,097,641 B1 | 8/2006 | Arless |
| 7,101,369 B2 | 9/2006 | Van der Weide |
| 7,115,126 B2 | 10/2006 | Berube |
| 7,128,739 B2 | 10/2006 | Prakash |
| 7,142,633 B2 | 11/2006 | Eberhard |
| 7,147,632 B2 | 12/2006 | Prakash |
| 7,153,298 B1 | 12/2006 | Cohen |
| 7,156,842 B2 | 1/2007 | Sartor |
| 7,160,289 B2 | 1/2007 | Cohen |
| 7,160,292 B2 | 1/2007 | Moorman |
| 7,182,762 B2 | 2/2007 | Bortkiewicz |
| 7,184,824 B2 | 2/2007 | Hashimshony |
| 7,197,363 B2 | 3/2007 | Prakash |
| 7,233,820 B2 | 6/2007 | Gilboa |
| 7,244,254 B2 | 7/2007 | Brace |
| 7,263,997 B2 | 9/2007 | Madsen et al. |
| 7,266,407 B2 | 9/2007 | Li et al. |
| 7,282,049 B2 | 10/2007 | Orszulak |
| 7,311,703 B2 | 12/2007 | Turovskiy |
| 7,318,824 B2 | 1/2008 | Prakash |
| 7,324,104 B1 | 1/2008 | Bitter |
| 7,331,960 B2 | 2/2008 | Schaer |
| 7,381,208 B2 | 6/2008 | Van der Walt |
| 7,400,929 B2 | 7/2008 | Zelickson et al. |
| 7,402,140 B2 | 7/2008 | Spero |
| 7,410,484 B2 | 8/2008 | Littrup |
| 7,467,015 B2 | 12/2008 | Van der Weide |
| 7,473,219 B1 | 1/2009 | Glenn |
| 7,527,623 B2 | 5/2009 | Prakash |
| 7,594,313 B2 | 9/2009 | Prakash |
| 7,601,149 B2 | 10/2009 | DiCarlo |
| 7,625,369 B2 | 12/2009 | Abboud |
| 7,722,620 B2 | 5/2010 | Truckai |
| 7,731,677 B2 | 6/2010 | Sakurai |
| 7,815,637 B2 | 10/2010 | Ormsby |
| 7,826,904 B2 | 11/2010 | Appling |
| 7,862,559 B2 | 1/2011 | Prakash |
| 7,875,024 B2 | 1/2011 | Turovskiy |
| 8,059,059 B2 | 1/2011 | Bonn |
| 8,035,570 B2 | 10/2011 | Prakash |
| 8,093,500 B2 | 1/2012 | Deborski |
| 8,109,895 B2 | 2/2012 | Williams et al. |
| 8,147,511 B2 | 4/2012 | Perry |
| 8,152,799 B2 | 4/2012 | Ormsby |
| 8,155,418 B2 | 4/2012 | Delso |
| 8,235,981 B2 | 8/2012 | Prakash |
| 8,357,148 B2 | 1/2013 | Boulais et al. |
| 8,403,924 B2 | 3/2013 | Behnke |
| 8,430,871 B2 | 4/2013 | Brannan |
| 8,454,589 B2 | 6/2013 | Deno |
| 8,515,554 B2 | 8/2013 | Carr |
| 8,523,854 B2 | 9/2013 | Willyard |
| 8,540,710 B2 | 9/2013 | Johnson |
| 8,574,227 B2 | 11/2013 | Hancock |
| 8,643,561 B2 | 2/2014 | Prakash |
| 8,653,828 B2 | 2/2014 | Hancock |
| 8,655,454 B2 | 2/2014 | Prakash |
| 8,672,932 B2 | 3/2014 | van der Weide |
| 8,747,398 B2 | 6/2014 | Behnke |
| 8,764,744 B2 | 7/2014 | Brannan |
| 8,932,281 B2 | 1/2015 | Brannan |
| 8,934,989 B2 | 1/2015 | Ormsby |
| 8,945,111 B2 | 2/2015 | Brannan et al. |
| 8,968,290 B2 | 3/2015 | Brannan |
| 9,008,793 B1 | 4/2015 | Cosman |
| 9,011,421 B2 | 4/2015 | Brannan |
| 9,017,319 B2 | 4/2015 | Brannan |
| 9,041,616 B2 | 5/2015 | Prakash |
| 9,072,532 B2 | 7/2015 | van der Weide |
| 9,113,926 B2 | 8/2015 | Brannan |
| 9,119,649 B2 | 9/2015 | van der Weide |
| 9,119,650 B2 | 9/2015 | Brannan |
| 9,161,811 B2 | 10/2015 | Cronin |
| 9,173,706 B2 | 11/2015 | Rossetto |
| 9,192,436 B2 | 11/2015 | Willyard |
| 9,192,438 B2 | 11/2015 | Thiel |
| 9,198,725 B2 | 12/2015 | Willyard |
| 9,220,441 B2 | 12/2015 | Yoo |

(56) References Cited

U.S. PATENT DOCUMENTS

| | | |
|---|---|---|
| 2001/0020166 A1 | 9/2001 | Daly et al. |
| 2001/0049524 A1 | 9/2001 | Morgan et al. |
| 2001/0039416 A1 | 11/2001 | Moorman et al. |
| 2002/0022836 A1 | 2/2002 | Goble |
| 2002/0026187 A1 | 2/2002 | Swanson et al. |
| 2002/0026188 A1 | 2/2002 | Balbierz et al. |
| 2002/0040185 A1 | 4/2002 | Atalar et al. |
| 2002/0072742 A1 | 6/2002 | Schaefer |
| 2002/0087151 A1 | 7/2002 | Mody |
| 2002/0087157 A1 | 7/2002 | Sliwa et al. |
| 2002/0173780 A1 | 11/2002 | Altshuler |
| 2002/0183740 A1 | 12/2002 | Edwards |
| 2003/0032951 A1 | 2/2003 | Rittman et al. |
| 2003/0060813 A1 | 3/2003 | Loeb |
| 2003/0065317 A1 | 4/2003 | Rudie |
| 2003/0088242 A1 | 5/2003 | Prakash |
| 2003/0120268 A1 | 6/2003 | Bertolero |
| 2003/0130711 A1 | 7/2003 | Pearson et al. |
| 2004/0030367 A1 | 2/2004 | Yamaki et al. |
| 2004/0068208 A1 | 4/2004 | Cimino et al. |
| 2004/0082859 A1 | 4/2004 | Schaer |
| 2004/0116921 A1 | 6/2004 | Sherman |
| 2004/0133254 A1 | 7/2004 | Sterzer |
| 2004/0158237 A1 | 8/2004 | Abboud |
| 2004/0186517 A1 | 9/2004 | Hill et al. |
| 2004/0199154 A1 | 10/2004 | Nahon |
| 2004/0215131 A1 | 10/2004 | Sakurai et al. |
| 2004/0215294 A1 | 10/2004 | Littrup et al. |
| 2004/0243004 A1 | 12/2004 | Carr |
| 2004/0243200 A1 | 12/2004 | Turner |
| 2004/0267248 A1 | 12/2004 | Duong |
| 2005/0011885 A1 | 1/2005 | Seghatol |
| 2005/0015081 A1 | 1/2005 | Turovskiy |
| 2005/0075629 A1 | 4/2005 | Chapelon |
| 2005/0107870 A1 | 5/2005 | Wang |
| 2005/0109900 A1 | 5/2005 | Schilt et al. |
| 2005/0113824 A1 | 5/2005 | Sartor |
| 2005/0143726 A1 | 6/2005 | Bortkiewicz |
| 2005/0149010 A1 | 7/2005 | Turovskiy |
| 2005/0165389 A1 | 7/2005 | Swain |
| 2005/0177209 A1 | 8/2005 | Leung et al. |
| 2005/0245919 A1 | 11/2005 | van der Weide |
| 2005/0245920 A1 | 11/2005 | Vitullo et al. |
| 2006/0064083 A1 | 3/2006 | Khalaj et al. |
| 2006/0079886 A1 | 4/2006 | Orszulak |
| 2006/0094956 A1 | 5/2006 | Viswanathan |
| 2006/0106281 A1 | 5/2006 | Boulais |
| 2006/0122625 A1 | 6/2006 | Truckai |
| 2006/0129140 A1 | 6/2006 | Todd et al. |
| 2006/0155270 A1 | 7/2006 | Hancock |
| 2006/0171506 A1 | 8/2006 | Lovoi et al. |
| 2006/0189973 A1 | 8/2006 | van der Weide |
| 2006/0200026 A1 | 9/2006 | Wallace et al. |
| 2006/0200120 A1 | 9/2006 | DiCarlo |
| 2006/0224220 A1 | 10/2006 | Zelickson |
| 2006/0264921 A1 | 11/2006 | Deutsch |
| 2006/0276780 A1 | 12/2006 | Brace |
| 2006/0289528 A1 | 12/2006 | Chiu |
| 2007/0016180 A1 | 1/2007 | Lee, Jr. et al. |
| 2007/0021741 A1 | 1/2007 | Marwan et al. |
| 2007/0066972 A1 | 3/2007 | Ormsby |
| 2007/0185554 A1 | 8/2007 | Appling et al. |
| 2007/0203551 A1 | 8/2007 | Cronin |
| 2007/0208389 A1 | 9/2007 | Amundson et al. |
| 2007/0230757 A1 | 10/2007 | Trachtenberg et al. |
| 2007/0270924 A1 | 11/2007 | McCann et al. |
| 2007/0276362 A1 | 11/2007 | Rioux |
| 2007/0282319 A1 | 12/2007 | van der Weide |
| 2007/0288079 A1 | 12/2007 | van der Weide |
| 2008/0033424 A1 | 2/2008 | Van Der Weide |
| 2008/0045938 A1 | 2/2008 | Weide et al. |
| 2008/0058785 A1* | 3/2008 | Boyden ............... A61B 5/0071 606/13 |
| 2008/0114345 A1 | 5/2008 | Arless et al. |
| 2008/0147056 A1 | 6/2008 | Van der Weide |
| 2008/0161890 A1 | 7/2008 | Lafontaine |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0195226 A1 | 8/2008 | Williams et al. |
| 2008/0221391 A1 | 9/2008 | Weitzner et al. |
| 2008/0243176 A1 | 10/2008 | Weitzner et al. |
| 2009/0005766 A1 | 1/2009 | Brannan |
| 2009/0054962 A1 | 2/2009 | Lefler |
| 2009/0076492 A1 | 3/2009 | Behnke |
| 2009/0118725 A1 | 5/2009 | Auth et al. |
| 2009/0187180 A1 | 7/2009 | Brannan |
| 2009/0187186 A1 | 7/2009 | Jakus |
| 2009/0196480 A1* | 8/2009 | Nields ................ G06T 7/33 382/132 |
| 2009/0222002 A1 | 9/2009 | Bonn et al. |
| 2009/0281536 A1 | 11/2009 | Beckman et al. |
| 2009/0306644 A1 | 12/2009 | Mayse et al. |
| 2010/0023866 A1 | 1/2010 | Peck |
| 2010/0045558 A1 | 2/2010 | Rossetto |
| 2010/0045559 A1 | 2/2010 | Rossetto |
| 2010/0076424 A1 | 3/2010 | Carr |
| 2010/0081928 A1 | 4/2010 | Hyde et al. |
| 2010/0137796 A1 | 6/2010 | Perry et al. |
| 2010/0228244 A1 | 9/2010 | Hancock |
| 2010/0268223 A1 | 10/2010 | Coe |
| 2010/0286791 A1 | 11/2010 | Goldsmith |
| 2010/0292766 A1 | 11/2010 | Duong |
| 2010/0305561 A1 | 12/2010 | Prakash et al. |
| 2010/0312095 A1 | 12/2010 | Jenkins |
| 2010/0312096 A1 | 12/2010 | Guttman |
| 2010/0317962 A1 | 12/2010 | Jenkins |
| 2011/0077635 A1 | 3/2011 | Bonn et al. |
| 2011/0098696 A1 | 4/2011 | Brannan |
| 2011/0118723 A1 | 5/2011 | Turner et al. |
| 2011/0118725 A1 | 5/2011 | Mayse |
| 2011/0213352 A1 | 9/2011 | Lee et al. |
| 2011/0238060 A1 | 9/2011 | Lee, Jr. |
| 2011/0238061 A1 | 9/2011 | van der Weide |
| 2011/0257647 A1 | 10/2011 | Mayse |
| 2011/0301587 A1 | 12/2011 | Deem |
| 2012/0016358 A1 | 1/2012 | Mayse |
| 2012/0053577 A1 | 3/2012 | Lee et al. |
| 2012/0116286 A1 | 5/2012 | Williams et al. |
| 2012/0182134 A1 | 7/2012 | Doyle |
| 2012/0194409 A1 | 8/2012 | Brannan |
| 2012/0203216 A1 | 8/2012 | Mayse |
| 2012/0203222 A1 | 8/2012 | Mayse |
| 2012/0209257 A1 | 8/2012 | Weide et al. |
| 2012/0209261 A1 | 8/2012 | Mayse |
| 2012/0209296 A1 | 8/2012 | Mayse |
| 2012/0232544 A1 | 9/2012 | Willyard |
| 2012/0232549 A1 | 9/2012 | Willyard |
| 2012/0310228 A1 | 12/2012 | Bonn et al. |
| 2012/0316551 A1 | 12/2012 | van der Weide |
| 2012/0316552 A1 | 12/2012 | Mayse |
| 2012/0316559 A1 | 12/2012 | Mayse |
| 2013/0004037 A1 | 1/2013 | Scheuering |
| 2013/0023866 A1 | 1/2013 | Stringham et al. |
| 2013/0072924 A1 | 3/2013 | Burgener |
| 2013/0116679 A1 | 5/2013 | van der Weide et al. |
| 2013/0123598 A1 | 5/2013 | Jenkins |
| 2013/0131496 A1 | 5/2013 | Jenkins |
| 2013/0165915 A1 | 6/2013 | Thiel |
| 2013/0259335 A1* | 10/2013 | Mallya .............. G06T 7/0012 382/128 |
| 2013/0306543 A1 | 11/2013 | Beisser |
| 2013/0338530 A1 | 12/2013 | Kassab |
| 2014/0005706 A1 | 1/2014 | Gelfand et al. |
| 2014/0046176 A1 | 2/2014 | Ladtkow et al. |
| 2014/0152656 A1 | 6/2014 | Yoo et al. |
| 2014/0163664 A1 | 6/2014 | Goldsmith |
| 2014/0276033 A1 | 9/2014 | Brannan et al. |
| 2014/0276200 A1 | 9/2014 | Brannan et al. |
| 2014/0046174 A1 | 12/2014 | Ladtkow et al. |
| 2015/0148792 A1 | 5/2015 | Kim et al. |
| 2015/0150628 A1 | 6/2015 | Buysse et al. |
| 2015/0164587 A1 | 6/2015 | Bonn et al. |

(56) References Cited

U.S. PATENT DOCUMENTS

| | | |
|---|---|---|
| 2015/0190193 A1 | 7/2015 | Mayse et al. |
| 2015/0250540 A1 | 9/2015 | Behdad et al. |
| 2015/0351839 A1 | 12/2015 | Brannan |
| 2015/0374438 A1 | 12/2015 | van der Weide |

FOREIGN PATENT DOCUMENTS

| | | |
|---|---|---|
| CN | 1593353 | 3/2005 |
| CN | 1703168 | 11/2005 |
| CN | 2753408 | 1/2006 |
| CN | 201267529 | 7/2009 |
| CN | 101511295 | 8/2009 |
| CN | 101563042 | 10/2009 |
| EP | 1186274 | 3/2002 |
| EP | 1265532 | 12/2002 |
| EP | 1395190 | 3/2004 |
| EP | 1450710 | 9/2004 |
| EP | 1499251 | 1/2005 |
| EP | 1542607 | 6/2005 |
| EP | 1723922 | 11/2006 |
| EP | 2098184 | 9/2009 |
| EP | 2295000 | 3/2011 |
| EP | 2316370 | 5/2011 |
| EP | 1659969 | 10/2012 |
| GB | 2388039 | 11/2003 |
| GB | 2406521 | 4/2005 |
| JP | 10-192286 | 7/1998 |
| JP | 2002-541884 | 12/2002 |
| JP | 2003-530139 | 10/2003 |
| JP | 2003-534037 | 11/2003 |
| JP | 2004-188179 | 7/2004 |
| JP | 2005-522274 | 7/2005 |
| JP | 2007-029457 | 2/2007 |
| JP | 2007-532024 | 11/2007 |
| JP | 2008-142467 | 6/2008 |
| JP | 2009-006150 | 1/2009 |
| JP | 2009-521264 | 6/2009 |
| JP | 2009-521967 | 6/2009 |
| JP | 2009-207898 | 9/2009 |
| JP | 2009-285463 | 12/2009 |
| JP | 2010-505573 | 2/2010 |
| JP | 2010-050975 | 3/2010 |
| JP | 2011-511538 | 4/2011 |
| JP | 2011-092720 | 5/2011 |
| JP | 2011-152414 | 8/2011 |
| WO | WO 1992/004934 | 4/1992 |
| WO | WO 1993/009845 | 5/1993 |
| WO | WO 1995/004385 | 9/1995 |
| WO | WO 1997/048449 | 12/1997 |
| WO | WO 1999/056643 | 11/1999 |
| WO | WO 2000/057811 | 10/2000 |
| WO | WO 2001/070114 | 9/2001 |
| WO | WO 2003/039385 | 5/2003 |
| WO | 2003/086190 | 10/2003 |
| WO | WO 2003/086498 | 10/2003 |
| WO | WO 2003/088806 | 10/2003 |
| WO | WO 2003/088858 | 10/2003 |
| WO | WO 2004/004586 | 1/2004 |
| WO | WO 2004/026122 | 1/2004 |
| WO | WO 2004/033039 | 4/2004 |
| WO | WO 2004/084748 | 10/2004 |
| WO | WO 2004/112628 | 12/2004 |
| WO | WO 2005/011049 | 2/2005 |
| WO | WO 2005/034783 | 4/2005 |
| WO | WO 2005/110265 | 11/2005 |
| WO | WO 2006/002843 | 1/2006 |
| WO | WO 2006/002943 | 1/2006 |
| WO | WO 2006/004585 | 1/2006 |
| WO | WO 2006/005579 | 1/2006 |
| WO | WO 2006/008481 | 1/2006 |
| WO | WO 2006/084676 | 8/2006 |
| WO | WO 2006/122149 | 11/2006 |
| WO | WO 2006/127847 | 11/2006 |
| WO | WO 2007/076924 | 7/2007 |
| WO | WO 2007/112103 | 10/2007 |
| WO | WO 2008/008545 | 1/2008 |
| WO | WO 2008/044013 | 4/2008 |
| WO | WO 2008/142686 | 11/2008 |
| WO | WO 2010/067360 | 6/2010 |
| WO | WO 2011/008903 | 1/2011 |
| WO | WO 2011/017168 | 2/2011 |
| WO | WO 2011/140087 | 11/2011 |
| WO | WO 2013/173481 | 11/2013 |

OTHER PUBLICATIONS

International Search Report & Written Opinion, International Patent Application No. PCT/US2017/027424, dated Oct. 9, 2017.
Brace, C. et al 'Analysis and experimental validation of triaxial antenna for microwave tumor ablation' IEEE MTTS Int Microw Symp Jun. 3, 2004 (6-11) 1437-1440.
Brace, C. et al 'Microwave Ablation with Triaxial Antenna: Results in ex vivo Bovine Liver' IEEE Transactions on Microwave Theory and Techniques, vol. 53, No. 1 Jan. 2005.
English translation of Decision of Refusal from related Japanese Patent Application No. 2013-509179, dated Jun. 30, 2015.
Golio, 'The RF and microwave handbook' Edition 2 Published by CRC Press 2001 ISBN 0849338592X, 97808493859626.
Guy, AW (1971) IEEE Trans. Microwave Theory Tech. 19 pp. 189-217.
Head, H.W. et al 'Thermal Ablation for Hepatocellular Carcinoma' Gastroenterology (2004) 127 pp. S167-S178.
Seki, T. et al 'Ultrasonically Guided Percutaneous Microwave Coagulation Therapy for Small Hepatocellular Carcinoma' Cancer, Aug. 1, 1994, vol. 74, No. 3 pp. 817-825.
"Carbon dioxide." Carbon dioxide—New World Encyclopedia. Web. <http://www.newworldencyclopedia.org/entry/Carbon_dioxide>.
European Search Report dated Mar. 3, 2009, EP Patent Application No. 06802385.2.
Extended European Search Report re: 11778168 dated Sep. 24, 2013.
International Patent Application No. PCT/US05/14534 dated Nov. 29, 2005; provided as WO 2006/004585.
International Preliminary Report on Patentability re: PCT/US2007/007464 dated Sep. 30, 2008.
International Search Report PCT/US2005/014534 dated Nov. 29, 2005.
International Search Report PCT/US2006/017981 dated Sep. 7, 2006.
International Search Report PCT US/2006/028821 dated Mar. 21, 2007.
International Search Report PCT/US2006/031644 dated Aug. 17, 2007.
International Search Report PCT/US2006/033341 dated Aug. 17, 2007.
International Search Report PCT/US2006/032811 dated Jan. 25, 2007.
International Search Report on Patentability re: PCT/US2007/016082 dated Jul. 21, 2008.
International Search Report PCT/US2011/035000 dated Jan. 6, 2012.
International Search Report re: PCT/US2012/071310 dated Feb. 25, 2013.
International Search Report re: PCT/US16/58888 dated Feb. 15, 2017.
International Search Report re: PCT/US2016/058890 dated Jan. 19, 2017.
International Preliminary Report on Patentability re: PCT/US2007/016082 dated Jan. 14, 2009.
International Preliminary Report on Patentability re: PCT/US2010/043558 dated Jan. 31, 2012.
International Preliminary Report on Patentability re: PCT/US2011/035000 dated Nov. 6, 2012.
International Preliminary Report on Patentability re: PCT/US2012/071310 dated Aug. 19, 2014.
Supplementary European Search Report re: EP07810483 dated Mar. 22, 2013.

(56) References Cited

OTHER PUBLICATIONS

Supplementary European Search Report re: EP10806929 dated Feb. 21, 2013.
Supplementary European Search Report re: EP11778168 dated Sep. 24, 2013.
Supplementary European Search Report re: EP12860249 dated Sep. 15, 2015.
U.S. Appl. No. 09/847,181, filed May 1, 2001.
U.S. Appl. No. 10/370,179, filed Feb. 19, 2003.
U.S. Appl. No. 10/834,802, filed Apr. 29, 2004.
U.S. Appl. No. 10/961,761, filed Oct. 7, 2004.
U.S. Appl. No. 10/961,994, filed Oct. 7, 2004.
U.S. Appl. No. 10/980,699, filed Nov. 3, 2004.
U.S. Appl. No. 11/053,987, filed Feb. 8, 2005.
U.S. Appl. No. 11/236,985, filed Sep. 28, 2005.
U.S. Appl. No. 11/237,136, filed Sep. 28, 2005.
U.S. Appl. No. 11/237,430, filed Sep. 28, 2005.
U.S. Appl. No. 11/440,331, filed May 24, 2006.
U.S. Appl. No. 11/452,637, filed Jun. 14, 2006.
U.S. Appl. No. 11/502,783, filed Aug. 11, 2006.
U.S. Appl. No. 11/514,628, filed Sep. 1, 2006.
U.S. Appl. No. 11/728,428, filed Mar. 26, 2007.
U.S. Appl. No. 11/728,457, filed Mar. 26, 2007.
U.S. Appl. No. 11/728,460, filed Mar. 26, 2007.
U.S. Appl. No. 60/679,722, filed May 10, 2005.
U.S. Appl. No. 60/785,466, filed Mar. 24, 2006.
U.S. Appl. No. 60/785,467, filed Mar. 24, 2006.
U.S. Appl. No. 60/785,690, filed Mar. 24, 2006.
U.S. Appl. No. 60/831,055, filed Jul. 14, 2006.
Guy, AW (1971) IEEE Trans. Microwave Theory Tech. 19 pp. 205-214.
European Search Report dated Mar. 9, 2015, EP Patent Application No. 14189493.1.
Extended European Search Report, EP Patent Application No. 11778168 dated Sep. 24, 2013.
Notice Regarding Extended European Search Report, EP Patent Application No. 11778168 dated Oct. 2, 2013.
International Preliminary Report on Patentability re: PCT/US2007/007408 dated Sep. 30, 2008.
International Preliminary Report on Patentability re: PCT/US2016/058888 dated Dec. 11, 2017.
International Preliminary Report on Patentability re: PCT/US2016/058890 dated May 11, 2018.
International Search Report re: PCT/US2007/007408 dated Aug. 31, 2007.
Extended European Search Report re: 17168163.8 dated Sep. 13, 2017.
International Patent Application No. PCT/US05/14534 dated Nov. 29, 2005.

\* cited by examiner

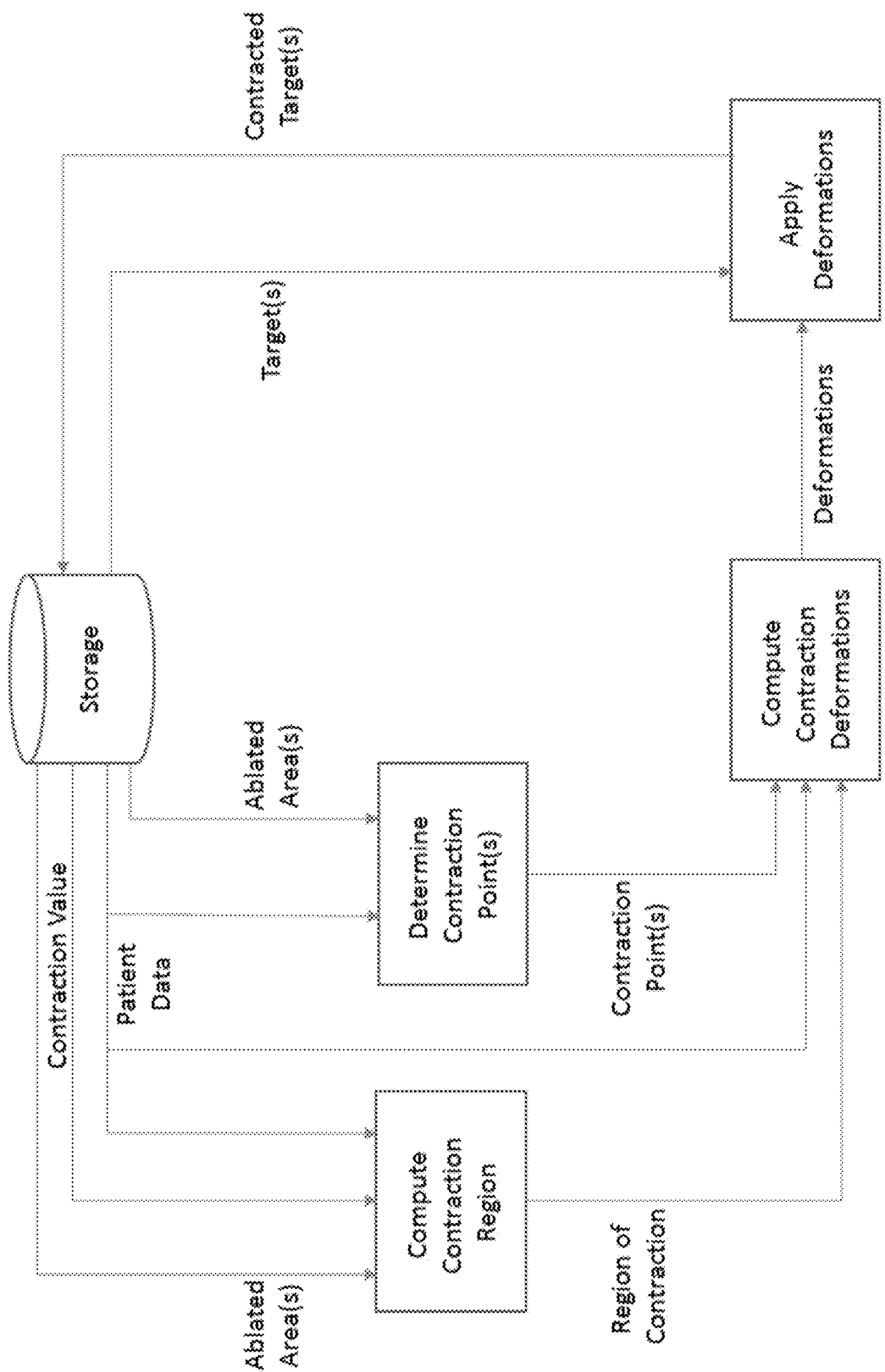

SYSTEMS AND METHODS FOR ENERGY DELIVERY

FIELD OF INVENTION

The present invention relates to comprehensive systems and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems and methods are provided for identifying and treating a target tissue region adjusting for ablation-related anatomical changes (e.g., tissue contraction).

BACKGROUND

Energy delivery devices (e.g., antennas, probes, electrodes, etc) (e.g., microwave ablation devices) (e.g., radiofrequency ablation devices) are used to deliver energy to a desired tissue region for purposes of "treating" a desired tissue region. Ablation therapy (e.g., microwave ablation, radiofrequency ablation) is a widely used, minimally invasive technique for the treatment of various conditions and/or disorders (e.g., tumor cells). Within such techniques, ablation energy (e.g., microwave energy) (e.g., radiofrequency energy) is used to heat a desired tissue region to a desired temperature to cause tissue destruction in the heated region.

The success of an ablation procedure is generally dependent upon maximizing the amount of desired tissue ablation and minimizing the amount of undesired tissue ablation. Such success is dependent upon the precise and accurate identification of a targeted tissue region, positioning of the energy delivery device at such an identified targeted tissue region, and delivery of such energy to the identified tissue region.

Improved techniques for accurately and precisely identifying a targeted tissue region targeted for an ablation procedure are needed.

The present invention addresses this need.

SUMMARY

Current techniques for identifying a targeted tissue region for an ablation procedure involve, for example, use of CT imaging or other imaging modalities. For example, CT imaging is used to locate and identify the specific anatomical region (e.g., three-dimensional anatomical dimension) to be ablated and based on that identified location, positioning of an energy delivery device at that identified location, and delivering ablation energy to the identified location.

A problem that limits the success for the ablation procedure, however, involves anatomical changes a targeted tissue region undergoes while being ablated. Indeed, the anatomical dimension of a tissue region undergoing an ablation procedure changes as the tissue region is ablated. For example, the anatomical dimension of a tissue region undergoes contraction during ablation which changes the pre and post procedure anatomical dimensions of the tissue region. Such anatomical changes that occur during the procedure (e.g., contraction) result in exposure of undesired tissue (e.g., healthy tissue) to the ablation energy. Such undesired ablation of non-targeted tissue not only compromises the success of the ablation procedure, but can result in serious adverse health consequences, particularly if the ablation zone is near healthy critical tissues or structures. If one attempts to compensate by selecting a smaller zone, one risks not destroying all of the intended tissue, which may make the treatment less efficacious, or in the case of tumor ablation, allow for tumor regrowth and metastasis.

The current techniques used to locate and identify the specific anatomical region (e.g., three-dimensional anatomical dimension) to be ablated (e.g., CT scan) fail to accommodate such anatomical changes (e.g., tissue contraction) as a targeted tissue region undergoes an ablation procedure.

The present invention provides systems, materials and methods that permit identification and location of a targeted tissue region that accommodates such anatomical changes (e.g., tissue contraction) as a targeted tissue region undergoes an ablation procedure.

In certain embodiments, the present invention provides systems comprising an energy delivery device and a processor, wherein the processor is configured to identify, select, and/or modify a target tissue region, adjusting for ablation-related anatomical changes.

In some embodiments, identifying the targeted tissue region adjusting for ablation-related anatomical changes comprises receiving information regarding the tissue region and the energy delivery device, computing a contraction region within the tissue region, determining expected contraction points within the tissue region, computing expected contraction deformations within the tissue region (e.g., determining the expected contraction distances (e.g., largest and smallest) and directions for each contraction point), applying the computed expected contraction deformations, and identifying and reporting the target tissue region adjusted for ablation-related anatomical changes.

In some embodiments, the processor is in communication with the energy delivery device. In some embodiments, the processor is configured to position the energy delivery device at a desired tissue region and/or to control energy delivery during an ablation procedure. In some embodiments, the desired tissue region is the identified target tissue region adjusted for ablation-related anatomical changes.

In some embodiments, the processor provides information regarding the contraction points to a user (e.g., via a processor based visual display; via wireless communication, etc.). For example, in some embodiments, the tissue region is provided along with the contraction points and the computed contraction point distances and directions for each point during the procedure (e.g., prior, after, and at any point during the procedure). In some embodiments, the minimum and maximum margin distances for the tissue region and each contraction point is provided.

In certain embodiments, the processor is configured to measure the smallest and largest distance between the target tissue region before and after ablation (e.g., ablation after contraction). In some embodiments, such measured distances are used to determine if desired margins are met during and following an ablation procedure.

In some embodiments, the processor is configured to quantify and compare the distance difference and/or direction difference between a targeted tissue region prior to adjustment for ablation-related anatomical changes and a targeted tissue region prior to adjustment for ablation-related anatomical changes. In some embodiments, the processor is configured to quantify and compare the actual distance difference and/or direction difference (e.g., prior to ablation procedure and post ablation procedure) between a targeted tissue region not adjusted for ablation-related anatomical changes and a targeted tissue region adjusted for ablation-related anatomical changes.

In certain embodiments, the processor is configured to monitor and/or control and/or provide feedback concerning one or more aspects during the ablation procedure. For example, in some embodiments, the processor is configured to monitor the predicted contraction point distance and direction for each contraction point during the ablation procedure. In some embodiments, the processor is configured to stop the ablation procedure if the predicted contraction point distance and/or direction for one or more contraction points is inconsistent with the actual respective contraction point distance and/or direction. In some embodiments, the processor is configured to adjust the amount of energy delivered (e.g., raise or lower) during the ablation procedure if the predicted contraction point distance and/or direction for one or more contraction points is inconsistent with the actual respective contraction point distance and/or direction. In some embodiments, the processor is configured to re-calculate contraction point distances and/or directions for one or more contraction points if the predicted contraction point distance and/or direction for one or more contraction points is inconsistent with the actual respective contraction point distance and/or direction. In some embodiments, the processor is configured to identify new contraction point and/or re-calculate contraction point distances and/or directions for one or more existing contraction points if the predicted contraction point distance and/or direction for one or more contraction points is inconsistent with the actual contraction point distance and/or direction for each contraction point. In some embodiments, processor is configured to make similar adjustments based upon differences in predicted versus actual temperature differences within the tissue region, predicted versus actual temperature differences in the energy delivery device, etc.

In some embodiments, the systems further comprise a power supply electrically connected to the energy delivery device.

In certain embodiments, the present invention provides methods for ablating a tissue region comprising providing such a system, identifying a target tissue region adjusted for ablation-related anatomical changes with the processor, positioning the energy delivery device at the identified targeted tissue region adjusted for ablation-related anatomical changes, and ablating the tissue region (e.g., and not ablating tissue outside of the target tissue region). In some embodiments, the target tissue region is identified and/or modified during an ablation procedure.

In some embodiments, tissue region is within a subject (e.g., a human subject).

In some embodiments, the tissue region ablated does not include tissue not included in the identified target tissue region adjusted for ablation-related anatomical changes.

BRIEF DESCRIPTION OF THE DRAWINGS

FIG. 1 shows a schematic of an exemplary process used for generating a target tissue region adjusting for ablation-related anatomical changes (e.g., tissue contraction).

DETAILED DESCRIPTION

Current techniques used to locate and identify a specific anatomical region (e.g., three-dimensional anatomical dimension) to be ablated (e.g., via CT scan) fail to accommodate for anatomical changes (e.g., tissue contraction) as a target tissue region undergoes an ablation procedure. Such anatomical changes result in undesired ablation of healthy tissue or otherwise cause over- or under-ablation of tissues, inconsistent with the goals of the procedure The present invention provides systems, materials and methods that permit identification, location, and ablation of a target tissue regions that accommodate such anatomical changes (e.g., tissue contraction) as a target tissue region undergoes an ablation procedure.

In some embodiments, a processor (e.g., computer) is used to identify and locate a target tissue region or regions from tissue imaging data that accommodate such anatomical changes (e.g., tissue contraction). In some embodiments, the processor uses software that assesses the presence and absence of variables associated with the tissue region to be ablated and variables associated with the type of energy delivery device and energy to be used during the procedure.

Examples of such variables associated with the tissue region to be ablated and variables associated with the type of energy delivery device and energy to be used during the procedure include, but are not limited to, the type of energy to be utilized during the procedure (e.g., microwave or radiofrequency, or both), the length of time for the procedure, the range of temperatures to be achieved during the procedure (e.g., temperate(s) at the tissue), the type of tissue region undergoing the procedure (e.g., liver, lung, heart, kidney, solid tumor, etc.), the temperature of the tissue region, the age of the subject, the overall health of the subject, etc.

In some embodiments, identification of a target tissue region involves computations based upon the input variables (e.g., variables associated with the tissue region to be ablated and variables associated with the type of energy delivery device and energy to be used during the procedure).

In some embodiments, such computations predict the amount and type of anatomical change the desired tissue region will undergo during a procedure based upon the inputted variable information.

In some embodiments, such computations involve determining contraction points, computing a contraction region, computing contraction deformations, applying such contraction deformations, and generating a target tissue region adjusting for ablation-related anatomical changes (e.g., tissue contraction).

Such assessments are not limited to a particular manner of determining contraction points and computing a contraction region. In some embodiments, the method determines the contraction points through computing an approximation of the total extent of the tissue region (e.g., organ tissue) which is contracted during the ablation procedure. The approximation may be morphological or based on the type of tissue and nearby structures. In some embodiments, the method computes the contraction region through utilizing the knowledge that at a point of contraction the tissue will contract the most and will reduce as a function of distance and direction from that point. In such embodiments, the method computes one or more points of contraction within the ablated area. The computation may be based on geometry of the ablated area or the positioning of the ablation probes.

Such methods are not limited to a particular manner of computing contraction deformations. In some embodiments, the method utilizes the knowledge that, due to the nature of the contraction, every location within the contraction region(s) is transformed to some degree, and that the amount of the transformation is a function of the distance and direction from a contraction point. In some embodiments, a computed contraction deformation could include a set distance and direction or could include multiple distances for multiple direction changes. The function may be geometric, based on the distance and direction from a contraction point, or physical, based on characteristics of the tissues at that location and structures in the region. In some embodiments, the actual contraction distance is predicted for each contraction point pre-ablation and post-ablation. In some embodiments, the actual contraction direction (including potentially multiple direction changes) is predicted for each contraction point pre-ablation and post-ablation. In some embodiments, both the actual contraction distance and direction (including potentially multiple direction changes) is predicted for each contraction point pre-ablation and post-ablation. For example, for a certain contraction point, the amount of contraction distance and direction (including potentially multiple direction changes) is measured. In some embodiments, the processor is configured to compare the predicted contraction distance and direction and the actual contraction distance and direction for each contraction point.

Those transformations may be described as deformations stored in a deformation grid. The deformation at each location may be described as a vector whose magnitude and direction describe the characteristics of the contraction. For example, in some embodiments, each element of the deformation grid may be defined by a vector which points in the direction of the contraction point and its magnitude may be defined as a linear function of the distance from the contraction point.

Such methods are not limited to a particular manner of applying the deformations. In some embodiments, this process applies the characteristics of the contraction, as described by the deformations, to the tissue region to be ablated. At each location within the ablation region, upon determination that it intersects the target, the amount of transformation from the deformation grid at that corresponding location is determined. In some embodiments, if the target does not intersect the ablation region, the magnitude of the transformation is applied a value (e.g., zero). In some embodiments, the dimensions of the tissue region to be ablated are adjusted based upon such adjustments (e.g., the tissue region is transformed to the new location based on the direction and magnitude of the transformation).

FIG. 1 shows a schematic of an exemplary method used to generate a target tissue region, adjusting for ablation-related anatomical changes (e.g., tissue contraction). As can be seen, the storage device (e.g., computer) receives information regarding the tissue region to be ablated and additional factors. Next, the system determines contraction points and computes a contraction region. Next, contraction deformations are computed based upon the determined contraction points and the computed contraction region. Finally, deformations are applied based upon the computed contraction deformations, and a target tissue region adjusting for ablation-related anatomical changes (e.g., tissue contraction) is generated.

In certain embodiments, the system communicates with the energy delivery device or an operator such that the energy delivery device is properly positioned at an identified target tissue region so as to effect an ablation that will ablate the desired tissue, accounting for tissue contraction caused by the ablation process.

In certain embodiments, the present invention provides systems for treating a tissue region within a subject. In some embodiments, such systems comprise a processor as described above (with associated software), and an energy delivery device or devices. In some embodiments, the processor is configured to communicate with the energy delivery device. In some embodiments, the systems further comprise an energy generator in communication with the energy delivery device.

In certain embodiments, the present invention provides systems for the delivery of ablation energy comprising a power supply, delivering power management system (e.g., a power splitter to control power delivery to two or more probes), a processor, an energy emitting device (e.g., ablation probe), a cooling system, an imaging system, a temperature monitoring system, and/or a procedure tracking system.

In certain embodiments, the processor is further configured to quantify and compare the distance and direction difference between a targeted tissue region prior to adjustment for ablation-related anatomical changes and a targeted tissue region prior to adjustment for ablation-related anatomical changes. Similarly, in some embodiments, the processor is configured to quantify and compare the actual distance and direction difference (e.g., prior to ablation procedure and post ablation procedure) between a targeted tissue region not adjusted for ablation-related anatomical changes and a targeted tissue region adjusted for ablation-related anatomical changes.

In certain embodiments, the processor provides information regarding the contraction points to a user (e.g., via a processor based visual display, via wireless communication, etc.). For example, in some embodiments, the tissue region is provided along with the contraction points and the computed contraction point distances and directions for each point during the procedure (e.g., prior, after, and at any point during the procedure). In some embodiments, the minimum and maximum margin distances and directions for the tissue region and each contraction point is provided.

In certain embodiments, the processor is configured to measure the smallest and largest distance between the target tissue region before and after ablation (e.g., ablation after contraction). In some embodiments, such measured distances are used to determine if desired margins are met during and following an ablation procedure.

In certain embodiments, the processor is configured to monitor and/or control and/or provide feedback concerning one or more aspects during the ablation procedure. For example, in some embodiments, the processor is configured to monitor the predicted contraction point distance and/or direction for each contraction point during the ablation procedure. In some embodiments, the processor is configured to stop the ablation procedure if the predicted contraction point distance and/or direction for one or more contraction points is inconsistent with the actual respective contraction point distance and/or direction. In some embodiments, the processor is configured to adjust the amount of energy delivered (e.g., raise or lower) during the ablation procedure if the predicted contraction point distance and/or direction for one or more contraction points is inconsistent with the actual respective contraction point distance and/or direction. In some embodiments, the processor is configured to re-calculate contraction point distances and/or directions for one or more contraction points if the predicted contraction point distance and/or direction for one or more contraction points is inconsistent with the actual respective contraction point distance and/or direction. In some embodiments, the processor is configured to identify new contraction points and/or re-calculate contraction point distances and/or directions for one or more existing contraction points if the predicted contraction point distance and/or direction for one or more contraction points is inconsistent with the actual contraction point distance and/or direction for each contraction point. In some embodiments, processor is configured to make similar adjustments based upon differences in predicted versus actual temperature differences within the tissue region, temperature differences in the energy delivery device, etc.

In certain embodiments, the processor is configured to measure the smallest and largest distance between the target tissue region before and after ablation (e.g., ablation after contraction). In some embodiments, such measured distances are used to determine if desired margins are met during and following an ablation procedure.

The systems of the present invention may be combined within various system/kit embodiments. For example, in some embodiments, systems comprising one or more or all of a computer having a processor, a generator, a power distribution system, and an energy applicator, along with any one or more accessory component (e.g., surgical instruments, temperature monitoring devices, etc.). Exemplary system components are described in U.S. Pat. Nos. 7,101,369, 9,072,532, 9,119,649, and 9,192,438 and U.S. Publ. No. 20130116679, each of which is herein incorporated by reference in its entirety.

The systems of the present invention may be used in any medical procedure involving delivery of energy (e.g., radiofrequency energy, microwave energy, laser, focused ultrasound, etc.) to a tissue region.

The systems are not limited to treating a particular type or kind of tissue region (e.g., brain, liver, heart, blood vessels, foot, lung, bone, etc.). In some embodiments, the systems find use in ablating tumor regions. Additional treatments include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, primary or metastatic tumors. In some embodiments, the surgical application comprises the control of hemorrhage (e.g. electrocautery). In some embodiments, the surgical application comprises tissue cutting or removal.

The energy delivery systems contemplate the use of any type of device configured to deliver (e.g., emit) energy (e.g., ablation device, surgical device, etc.) (see, e.g., U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961,761, 10/834,802, 10/370,179, 09/847,181; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385; each herein incorporated by reference in their entireties). Such devices include any and all medical, veterinary, and research applications devices configured for energy emission, as well as devices used in agricultural settings, manufacturing settings, mechanical settings, or any other application where energy is to be delivered.

In some embodiments, the energy delivery systems utilize processors that monitor and/or control and/or provide feedback concerning one or more of the components of the system. In some embodiments, the processor is provided within a computer module. For example, in some embodiments, the systems provide software for regulating the amount of microwave energy provided to a tissue region through monitoring one or more characteristics of the tissue region including, but not limited to, the size and shape of a target tissue, the temperature of the tissue region, and the like (e.g., through a feedback system) (see, e.g., U.S. patent application Ser. Nos. 11/728,460, 11/728,457, and 11/728,428; each of which is herein incorporated by reference in their entireties). In some embodiments, the software is configured to provide information (e.g., monitoring information) in real time. In some embodiments, the software is configured to interact with the energy delivery systems such that it is able to raise or lower (e.g., tune) the amount of energy delivered to a tissue region. In some embodiments, the software is designed to regulate coolant. In some embodiments, the type of tissue being treated (e.g., liver) is inputted into the software for purposes of allowing the processor to regulate (e.g., tune) the delivery of energy to the tissue region based upon pre-calibrated methods for that particular type of tissue region. In other embodiments, the processor generates a chart or diagram based upon a particular type of tissue region displaying characteristics useful to a user of the system. In some embodiments, the processor provides energy delivering algorithms for purposes of, for example, slowly ramping power to avoid tissue cracking due to rapid out-gassing created by high temperatures. In some embodiments, the processor allows a user to choose power, duration of treatment, different treatment algorithms for different tissue types, simultaneous application of power to the antennas in multiple antenna mode, switched power delivery between antennas, coherent and incoherent phasing, etc. In some embodiments, the processor is configured for the creation of a database of information (e.g., required energy levels, duration of treatment for a tissue region based on particular patient characteristics) pertaining to ablation treatments for a particular tissue region based upon previous treatments with similar or dissimilar patient characteristics. In some embodiments, the processor is operated by remote control.

In some embodiments, user interface software is provided for monitoring and/or operating the components of the energy delivery systems. In some embodiments, the user interface software is operated by a touch screen interface. In some embodiments, the user interface software may be implemented and operated within a sterile setting (e.g., a procedure room) or in a non-sterile setting. In some embodiments, the user interface software is implemented and operated within a procedure device hub (e.g., via a processor). In some embodiments, the user interface software is implemented and operated within a procedure cart (e.g., via a processor). The user interface software is not limited to particular functions. Examples of functions associated with the user interface software include, but are not limited to, tracking the number of uses per component within the energy delivery system (e.g., tracking the number of times an energy delivery device is used), providing and tracking real time temperatures of each component or parts of each component (e.g., providing real time temperature of different locations along an energy delivery device (e.g., at the handle, at the stick, at the tip)) (e.g., providing real time temperature of the cables associated with the energy delivery systems), providing and tracking real time temperature of the tissue being treated, providing an automatic shut off for the part or all of the energy delivery system (e.g., an emergency shut off), generation of reports based upon the data accumulated, for example, prior to, during and after a procedure, providing audible and/or visual alerts to a user (e.g., alerts indicating a procedure has begun and/or is finished, alerts indicating a temperature has reached an aberrant level, alerts indicating the length of the procedure has gone beyond a default, etc.).

In some embodiments, the energy delivery systems utilize imaging systems comprising imaging devices. The energy delivery systems are not limited to particular types of imaging devices (e.g., endoscopic devices, stereotactic computer assisted neurosurgical navigation devices, thermal sensor positioning systems, motion rate sensors, steering wire systems, intraprocedural ultrasound, interstitial ultrasound, microwave imaging, acoustic tomography, dual energy imaging, fluoroscopy, computerized tomography magnetic resonance imaging, nuclear medicine imaging devices triangulation imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579; each herein incorporated by reference in their entireties). In some embodiments, the systems utilize endoscopic cameras, imaging components, and/or navigation systems that permit or assist in placement, positioning, and/or monitoring of any of the items used with the energy systems of the present invention.

In some embodiments, the energy delivery systems utilize tuning elements for adjusting the amount of energy delivered to the tissue region. In some embodiments, the tuning element is manually adjusted by a user of the system. In some embodiments, a tuning system is incorporated into an energy delivery device so as to permit a user to adjust the energy delivery of the device as desired (see, e.g., U.S. Pat. Nos. 5,957,969, 5,405,346; each herein incorporated by reference in their entireties).

In some embodiments, the energy delivery systems utilize coolant systems so as to reduce undesired heating within and along an energy delivery device (e.g., tissue ablation catheter). The systems are not limited to a particular cooling system mechanism.

In some embodiments, the energy delivering systems utilize temperature monitoring systems. In some embodiments, temperature monitoring systems are used to monitor the temperature of an energy delivery device (e.g., with a temperature sensor). In some embodiments, temperature monitoring systems are used to monitor the temperature of a tissue region (e.g., tissue being treated, surrounding tissue). In some embodiments, the temperature monitoring systems are designed to communicate with a processor for purposes of providing temperature information to a user or to the processor to allow the processor to adjust the system appropriately.

The system may further employ one or more additional components that either directly or indirectly take advantage of or assist the features of the present invention. For example, in some embodiments, one or more monitoring devices are used to monitor and/or report the function of any one or more components of the system. Additionally, any medical device or system that might be used, directly or indirectly, in conjunction with the devices of the present invention may be included with the system. Such components include, but are not limited to, sterilization systems, devices, and components, other surgical, diagnostic, or monitoring devices or systems, computer equipment, handbooks, instructions, labels, and guidelines, robotic equipment, and the like.

The systems are not limited to particular uses. Indeed, the energy delivery systems of the present invention are designed for use in any setting wherein the emission of energy is applicable. Such uses include any and all medical, veterinary, and research applications. In addition, the systems and devices of the present invention may be used in agricultural settings, manufacturing settings, mechanical settings, or any other application where energy is to be delivered. In some embodiments, the systems are configured for open surgery, percutaneous, intravascular, intracardiac, endoscopic, intraluminal, laparoscopic, or surgical delivery of energy. In some embodiments, the energy delivery devices may be positioned within a patient's body through a catheter, through a surgically developed opening, and/or through a body orifice (e.g., mouth, ear, nose, eyes, vagina, penis, anus) (e.g., a N.O.T.E.S. procedure). In some embodiments, the systems are configured for delivery of energy to a target tissue or region.

The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the systems are configured for guided delivery, for example, by computerized tomography, ultrasound, magnetic resonance imaging, fluoroscopy, and the like.

In certain embodiments, the present invention provides methods of treating a tissue region, comprising providing a tissue region and a system described herein (e.g., an energy delivery device, and at least one of the following components: a processor utilizing an algorithm of the present invention, a power supply, a temperature monitor, an imager, a tuning system, and/or a temperature reduction system); identifying and locating a targeted tissue region adjusting for expected ablation-related anatomical changes (e.g., tissue contraction); positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung, large intestine, small intestine, brain, neck, bone, kidney, muscle, tendon, blood vessel, prostate, bladder, and spinal cord.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A system comprising an energy delivery device and a processor, wherein the processor is configured to identify a target tissue region adjusted for ablation-related anatomical changes,
    wherein identifying the target tissue region adjusted for expected ablation-related anatomical changes comprises:
    a) receiving information regarding the tissue region and the energy delivery device,
    b) computing a contraction region within the tissue region,
    c) determining contraction points within the tissue region,
    d) computing contraction deformations within the tissue region,
    e) applying the computed contraction deformations, and
    f) identifying the target tissue region adjusted for ablation-related anatomical changes.

2. The system of claim 1, wherein the processor is in communication with the energy delivery device.

3. The system of claim 2, wherein the processor is configured to guide positioning of the energy delivery device to a desired tissue region.

4. The system of claim 3, wherein the desired tissue region is the identified target tissue region.

5. The system of claim 1, further comprising a power supply electrically connected to the energy delivery device.

6. The system of claim 2, wherein the contraction deformations comprise contraction point distances and contraction point directions for each contraction point.

7. The system of claim 6, wherein the contraction point directions for each contraction point comprises one or more direction changes.

8. A method of ablating a tissue region comprising providing a system as described in claim 1, identifying a target tissue region adjusted for ablation-related anatomical changes, positioning the energy delivery device at the identified target tissue region, and ablating the tissue region.

9. The method of claim 8, wherein the tissue region is within a subject.

10. The method of claim 9, wherein the subject is a human subject.

11. The method of claim 8, wherein the ablated tissue region does not include tissue not included in the identified target tissue region.

* * * * *